(12) United States Patent
Hayter et al.

(10) Patent No.: US 6,780,645 B2
(45) Date of Patent: Aug. 24, 2004

(54) DIAGNOSTIC KIT WITH A MEMORY STORING TEST STRIP CALIBRATION CODES AND RELATED METHODS

(75) Inventors: Paul G. Hayter, Mountain View, CA (US); Manoj K. Sharma, Milpitas, CA (US); Timothy J. Ohara, Danville, CA (US); Darwin Poulos, Los Altos, CA (US); Maria Aquino, Fremont, CA (US)

(73) Assignee: Lifescan, Inc., Milpitas, CA (US)

( * ) Notice: Subject to any disclaimer, the term of this patent is extended or adjusted under 35 U.S.C. 154(b) by 24 days.

(21) Appl. No.: 10/224,888

(22) Filed: Aug. 21, 2002

(65) Prior Publication Data

US 2004/0038411 A1 Feb. 26, 2004

(51) Int. Cl.[7] .......................... G01N 31/00; G01N 33/66
(52) U.S. Cl. ............................... 436/8; 436/14; 436/69; 436/164; 422/55; 422/58; 422/61; 422/73; 435/14; 702/19
(58) Field of Search ............................... 436/8, 14, 16, 436/63, 69, 164; 422/61, 55, 58, 73; 435/13, 14, 810; 702/19, 22, 23, 32; 703/11, 12; 73/1.01, 1.03

(56) References Cited

U.S. PATENT DOCUMENTS

| | | |
|---|---|---|
| 5,126,952 A | 6/1992 | Weber et al. |
| 5,366,609 A | 11/1994 | White et al. |
| 5,489,414 A | 2/1996 | Schreiber et al. |

(List continued on next page.)

FOREIGN PATENT DOCUMENTS

| | | | |
|---|---|---|---|
| EP | 0840122 A | | 5/1998 |
| EP | 0880407 B1 | | 4/2002 |
| WO | 99/22236 | * | 5/1999 |
| WO | WO 01/57510 A2 | | 8/2001 |
| WO | WO 02/48707 A2 | | 6/2002 |

OTHER PUBLICATIONS

Riley, M.R. et al. "Matrix–Enhanced Calibration Procedure for Multivariate Calibration Models with Near–Infrared Spectra" Applied Spectroscopy, The Society for Applied Spectroscopy. Baltimore, US vol. 52, No. 10, Oct. 1998, pp. 1339–1347, XP000805981 ISSN: 0003–7028 "abstract, tables 11–V" p. 1341, col. 2, line 18–21 p. 1342, col. 2, para. 3* *p. 1347, col. 1, line 10–13*.

(List continued on next page.)

*Primary Examiner*—Maureen M. Wallenhorst

(57) ABSTRACT

A diagnostic kit for measuring a characteristic of a fluid sample includes a test strip (e.g., a disposable blood glucose test strip) and device (e.g., a hand-held meter) for measuring a property (e.g., an optical or electrochemical property) of the test strip. The device also calculates, based on the measured property of the test strip, a characteristic (e.g., blood glucose concentration or INR) of a fluid sample applied to the test strip. Stored in a memory of the device are test strip calibration codes that represent geometric regions (e.g., polygonal or hexagonal geometric regions) of a multi-dimensional calibration parameter space. The test strip calibration codes and geometric regions are distributed across the multi-dimensional calibration parameter space such that a quantization error of assigning one of test strip calibration codes to the test strip is optimally reduced. Also, a method for optimally associating test strip calibration codes to calibration parameters for use in such a diagnostic kit that includes first optimally distributing a plurality of test strip calibration codes and geometric regions represented thereby across a multi-dimensional calibration parameter space. The distribution is conducted such that a quantization error of assigning one of the test strip calibration codes to the test strip of the diagnostic kit is optimally reduced. The method also includes storing the distributed test strip calibration codes in a memory of the diagnostic kit.

31 Claims, 11 Drawing Sheets

U.S. PATENT DOCUMENTS

| | | | |
|---|---|---|---|
| 5,856,195 A | * | 1/1999 | Charlton et al. .............. 436/50 |
| 6,084,660 A | | 7/2000 | Shartle |
| 6,168,957 B1 | * | 1/2001 | Matzinger et al. .......... 436/518 |
| 6,261,519 B1 | | 7/2001 | Harding et al. |
| 6,377,894 B1 | * | 4/2002 | Deweese et al. .............. 702/22 |
| 6,514,460 B1 | * | 2/2003 | Fendrock ..................... 422/55 |
| 2002/0019707 A1 | * | 2/2002 | Cohen et al. ................. 702/30 |
| 2003/0207441 A1 | * | 11/2003 | Eyster et al. ............ 435/287.1 |

OTHER PUBLICATIONS

McShane, M.J. et al. "Variable Selection in Multivariate Calibration of a Spectroscopic Glucose Sensor" Applied Spectroscopy, The Society for Applied Spectroscopy. Baltimore, US, vol. 51, No. 10, Oct. 1, 1997, pp. 1559–1564, XP000774280 ISSN 0003–7028 *abstract; figures 3.5* * p. 1559, col. 2, para. 2,3*.

Huang J. et al. "A comparison of calibration methods based on calibration data size and robustness" Chemometrics and Intelligent Laboratory Systems, Elsevier Science Publishers B.V. Amsterdam, NL, vol. 62, No. 1, Apr. 28, 2002, pp. 25–35, XP004345359 ISSN 0169–7439 *abstract; figures 8, 10, 12; tables 3–5* * p. 26, para. 1.1* *p. 28. col. 1, line 26–col. 2, line 2*.

European Search Report dated Dec. 9, 2003 for European Patent Application 03255154.1.

* cited by examiner

DIAGNOSTIC KIT WITH A MEMORY STORING TEST STRIP CALIBRATION CODES AND RELATED METHODS

BACKGROUND OF THE INVENTION

1. Field of the Invention

The present invention relates, in general, to diagnostic kits for the measurement of a fluid sample characteristic and, in particular, to diagnostic kits that include test strip calibration codes and related methods.

2. Description of the Related Art

Typical diagnostic kits for the measurement of a fluid sample characteristic include a device, such as a hand-held meter, and a test strip (e.g., a disposable blood glucose test strip) to which a fluid sample is applied. The device and test strip are used in tandem to measure an analyte concentration(s) (e.g., blood glucose concentration) or other characteristic(s) (e.g., prothrombin time [PT] and/or International Normalization Ratio [INR]) of the fluid sample. The device typically measures a property or properties of the test strip (e.g., an optical reflectance, optical transmittance or an electrochemical property) and then employs an algorithm(s) to calculate the characteristic based on the measured property or properties. Such conventional diagnostic kits are described in, for example, U.S. Pat. No. 6,084,660, issued on Jul. 4, 2000 and U.S. Pat. No. 6,261,519, issued Jul. 17, 2001 and U.S. patent application Ser. No. 10/100,531, filed Mar. 14, 2002, each of which is hereby fully incorporated by reference, as well as PCT patent applications WO 0248707 A2 and WO 0157510 A2.

In order to account for lot-to-lot variation in the test strips of such diagnostic kits, it is commonplace for test strip lots to be calibrated during their manufacture. Such calibration typically includes the determination of calibration parameters and the assignment of a test strip calibration code, associated with those calibration parameters, to each of the test strip lots. For example, in order to assign a test strip calibration code to a lot of prothrombin test strips, coagulation and PT calibration parameters can be experimentally determined using orthogonal regression routines. In such orthogonal regression routines, the bias between experimental test results and reference test results is minimized using a sum of squares function by adjusting various calibration parameters. The result of such an orthogonal regression routine is a set of experimental calibration parameters. If these calibration coefficients were assigned as calibration codes, there would be infinite number of calibration codes. In order to make a finite and manageable number of calibration codes, the experimental calibration parameters are then shifted to coincide with the closest calibration parameters contained in a pre-defined calibration parameter table. A calibration code associated with the closest calibration parameters is subsequently assigned to the lot of prothrombin test strips.

Conventional techniques of assigning test strip calibration codes to a lot of test strips, such as the calibration technique described above with respect to prothrombin test strips, have the drawbacks of (i) employing a sum of squares function, which is unduly sensitive to extreme experimental results and (ii) assuming that the calibration parameters from the predefined calibration parameter table that are closest to the experimentally determined calibration parameters are the most optimal, which is not necessarily correct. Due to these drawbacks, the accuracy of results obtained using a diagnostic kit that employs test strip calibration codes that have been associated with calibration parameters (and therefore associated with test strip lots) using conventional techniques may not be optimal.

In addition, under certain circumstances, it can be desirable to re-calibrate a test strip lot to verify the previous assignment of a test strip calibration code thereto. However, if individual test strip calibration codes are associated with calibration parameters that are too closely spaced (i.e., calibration parameters separated by a small increment of resolution), it is possible that a test strip lot will be assigned a test strip calibration code upon recalibration that is different from the test strip calibration code previously assigned. This can occur since, even though the recalibration was performed correctly, a finite calibration error is associated with the recalibration. The possible inconsistency of assigning a different test strip calibration code upon recalibration complicates verification of the assignment of a test strip calibration code to a test strip lot.

When a diagnostic kit is used to measure a characteristic of a fluid sample, the test strip calibration code assigned to the test strip enables the device to obtain calibration parameters for use in calculating the characteristic. There are several techniques that can be employed to convey the test strip calibration code assigned to a test strip to the device. These techniques include using a button on the device to select a numeric test strip calibration code; insertion into the device of an integrated circuit with a test strip calibration code; insertion into the device of a strip with a test strip calibration code that employs passive electronic components (e.g., resistors); proximal telemetry; and the use of a bar code or Read Only Memory (ROM) integrated circuit (see, for example, U.S. Pat. No. 5,489,414, U.S. Pat. No. 5,366,609 and European Patent 0880407 B1). In general, the simplest and most inexpensive technique is for a user to convey a test strip calibration code to a device by depressing a calibration code button on the device. However, in order for this technique to be practical, it is desirable that the device employs a minimal number of test strip calibration codes (e.g., one hundred or less test strip calibration codes, and more preferably 50 or less test strip calibration codes). Otherwise, conveying the test strip calibration code to the device is cumbersome for the user and the likelihood of user error is unduly high. On the other hand, there must be a sufficient number of test strip calibration codes to maintain the overall accuracy of the diagnostic kit.

Still needed in the field, therefore, is diagnostic kit that enables the use of a minimal number of test strip calibration codes and that employs test strip calibration codes that are optimally associated with calibration parameters and, thus, also optimally associated with test strip lots. Also needed, therefore, is a method for optimally associating test strip calibration codes to calibration parameters.

SUMMARY OF THE INVENTION

The present invention provides a diagnostic kit that includes test strip calibration codes that are optimally associated with calibration parameters and that, therefore, enables the use of a minimal number of test strip calibration codes. Since the test strip calibration codes are optimally associated with the calibration parameters, the test strip calibration codes will also be optimally assigned to a test strip lot during test strip calibration.

In arriving at the present invention, it was recognized that each test strip calibration code represents a geometric region of a multi-dimensional calibration parameter space (e.g., a two-dimensional calibration parameter space). It was further recognized that the multi-dimensional calibration parameter space consists of several non-overlapping geometric regions each associated with a unique calibration code. It was also recognized that this distribution of calibration codes associated with each geometric region and the calibration code assignment introduces a "quantization error" that should be optimally reduced. Such a quantization error can also be viewed as the error that is introduced into a diagnostic kit's performance by assigning a test strip calibration code to a test strip that is not coincident with the measured calibration coefficients. It was additionally recognized that quantization error should not add considerable amount to the testing error associated with measuring the calibration coefficients.

It was also recognized that distributing the test strip calibration parameters and geometric regions across the multi-dimensional calibration parameter space such that the quantization error is optimally reduced to the extent of testing error in measuring the calibration coefficients provides the most efficient arrangement. Such an efficient arrangement enables the use of a minimal number of test strip calibration codes and an optimal association of test strip calibration codes to calibration parameters. In addition, by minimizing overlap through understanding the uncertainty in measuring the calibration parameters due to testing error, the possibility of assigning a different test strip calibration code to a particular test strip lot during re-calibration is also minimized. This can occur since the geometric region associated with each calibration code can represent an area equivalent to that covered by the uncertainty in measuring the calibration codes.

It was further recognized that the increment of resolution between test strip calibration codes and the boundary of the geometric region represented by a test strip calibration code define the number of test strip calibration codes within the multi-dimensional calibration parameter space. This increment of resolution can, for example, be limited at the upper end by a diagnostic kit's overall accuracy requirements. If the increment of resolution is too large, the quantization error attributed to the assignment of test strip calibration codes to calibration parameters is undesirably large. However, when the increment of resolution is too small (e.g., when calibration error is larger than the increment of resolution), an unnecessarily large number of calibration codes results and recalibration inconsistency can occur.

For the reasons discussed above, diagnostic kits according to the present invention include test strip calibration codes and geometric regions that have been optimally distributed across a multi-dimensional calibration parameter space. Such optimization involves properly defining an increment of resolution for the test strip calibration codes and the shape (e.g., boundary) of the geometric region represented by each test strip calibration code in order to optimally reduce quantization error while minimizing the number of test strip calibration codes. Examples of suitable geometric regions are hexagons, parallelograms, rectangles, and other like polygonal structures.

A diagnostic kit for measuring a characteristic of a fluid sample according to an exemplary embodiment of the present invention includes a test strip and device (such as a hand-held meter) for measuring a property or properties (e.g., an optical or electrochemical property) of the test strip. The device also calculates a characteristic (e.g., PT and INR) of a fluid sample applied to the test strip, based on the measured property or properties of the test strip.

The device includes a memory with a plurality of test strip calibration codes stored therein. Each of the plurality of test strip calibration codes stored in the memory represents a geometric region of a multi-dimensional calibration parameter space. In addition, the plurality of test strip calibration codes and geometric regions are distributed across the multi-dimensional calibration parameter space such that a quantization error of assigning one of the plurality of test strip calibration codes to the test strip is optimally reduced.

The optimal reduction of the quantization error can include, for example, optimizing the distribution of test strip calibration codes and the shape of the geometric region represented by each test strip calibration code such that a minimum number of test strip calibration codes are stored in the memory while maintaining predetermined quantization error limits. The predetermined quantization error limits employed during optimization can, for example, be based on overall diagnostic kit accuracy requirements and an assessment of testing error in measuring the calibration coefficients. For example, the quantization error limits can be based on a fraction (e.g., one fifth or one twentieth) of the overall diagnostic kit accuracy requirements.

Since the test strip calibration codes and geometric regions are distributed based on optimally reducing the quantization error and in a manner directly related to accuracy requirements, calibration parameters are not necessarily associated with their closest test strip calibration code. This is beneficial since, depending on the diagnostic kit, diagnostic kit performance accuracy can be optimized by not assigning the closest neighboring test strip calibration parameter as particular combinations of calibration parameters can have a self-compensating effect.

Also provided by the present invention is a method for optimally associating test strip calibration codes to calibration parameters for use in a diagnostic kit that includes a test strip and a device with a memory. The method includes optimally distributing a plurality of test strip calibration codes, and geometric regions represented thereby, across a calibration parameter space such that a quantization error of assigning one of the plurality of test strip calibration codes to the test strip is optimally reduced. The plurality of test strip calibration codes that have been thus distributed are then stored in a memory of the diagnostic kit.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings, of which.

DESCRIPTION OF EXEMPLARY EMBODIMENTS OF THE INVENTION

To be consistent throughout the present specification and for clear understanding of the present invention, the following definition is hereby provided for a term used therein:

The term "quantization error" refers to the error associated with assigning a test strip calibration code to a test strip that is not coincident with the measured calibration coefficients. Such a quantization error is asymmetrically dependent upon the distribution of test strip calibration codes, and the geometric regions represented by the test strip calibration codes, across a multi-dimensional calibration parameter space. Therefore, the quantization error can also be viewed as the error associated with having a test strip calibration code represent an entire geometric region of a multi-dimensional calibration parameter space. Depending on the context, the quantization error can also be referred to as the calibration error.

Figure 1:
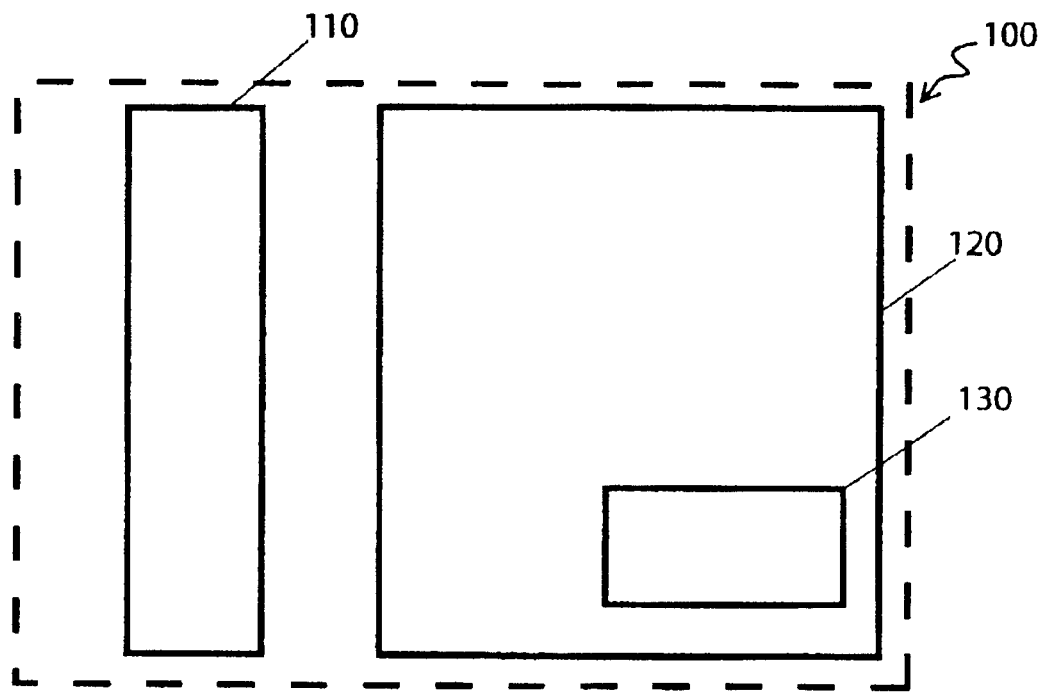
FIG. 1 is a simplified block diagram of a diagnostic kit according to an exemplary embodiment of the present invention.

FIG. 1 is a simplified block diagram illustrating a diagnostic kit 100 (encompassed within the dashed lines) for measuring a characteristic of a fluid sample. Diagnostic kit 100 includes a test strip 110 and a device 120 (e.g., a hand-held meter) for measuring a property of test strip 100 and calculating, therefrom, the characteristic of the fluid sample.

One skilled in the art will recognize that diagnostic kits according to the present invention can be adapted for use with a variety of samples, fluid or otherwise, including biological samples such as tissues and feces. In addition, it is contemplated that embodiments of the invention can be adapted to a range of assay kits, biological or otherwise, known to those skilled in the art. Suitable assay kits include those employed in DNA sequencing, protein analysis, drug discovery and pharmaceutical development. Such suitable assay kits include reagent(s) (e.g., liquid reagents and lypholized reagents) and an analytical device employed in conjunction with the reagent(s) to carry out a predetermined analysis of a sample. Once apprised of the present invention, it will be recognized that the accuracy of results obtained with such assay kits can be improved through the use of reagent calibration codes. Moreover, a memory included in the analytical device can have a plurality of reagent calibration codes stored therein with each of the reagent calibration codes representing a geometric region of a calibration parameter space. Furthermore, such reagent calibration codes and geometric regions can be distributed across the calibration parameter space such that a quantization error of assigning one of the reagent calibration codes to the reagent is optimally reduced.

Diagnostic kits in accordance with the present invention can be employed to measure any characteristic of a fluid sample known to one skilled in the art, including, but not limited to, the concentration of certain analytes in fluid samples applied to test strip 110 and/or chemical properties (e.g., pH or alkalinity) of a fluid sample applied to test strip 110. Glucose, cholesterol, proteins, ketones, phenylalanine and enzymes in a physiological fluid such as blood, urine or saliva are examples of such analytes, while a prothrombin-time (PT) of a blood sample is an example of such a chemical property.

Device 120 can measure, for example, an optical property and/or electrochemical property of test strip 110 and calculate, based on the measured property, a characteristic of a fluid sample applied to the test strip. Such a calculation can be accomplished, for example, using an algorithm(s) that employs both the measured property (or measured properties) of the test strip and calibration parameters. In this regard, a test strip calibration code previously assigned to test strip 110 and conveyed to device 120 serves to identify appropriate calibration parameters for use in the algorithm (s). One skilled in the art will recognize that the algorithm can be conventionally implemented by software and hardware included in device 120.

Device 120 also includes a memory 130 with a plurality of test strip calibration codes stored therein. Each of the test strip calibration codes stored in memory 130 represents a geometric region of a multi-dimensional calibration parameter space. Furthermore, each calibration code is associated with a set of calibration parameters that can be employed in an algorithm(s) for calculating the fluid sample characteristic. Memory 130 can be any type of memory known to one skilled in the art, including, but not limited, to memories based on integrated circuits (e.g., Dynamic Random Access Memories [DRAM], Static Random Access Memories [SRAM], programmable read-only memory or hard-wired logic) and disk-based memories.

In diagnostic kits according to the present invention, the plurality of test strip calibration codes and the geometric regions represented by the test strip calibration codes are distributed across the multi-dimensional calibration parameter space such that a quantization error of assigning a test strip calibration code to the test strip is optimally reduced. Such an optimal reduction can be accomplished, for example, through a statistical analysis based on the algorithm(s) used by the device to calculate the fluid sample characteristic, an objective function that represents test strip accuracy, the variation in the measurement of calibration coefficients, and balancing the error associated with the variation in measurement of calibration coefficients with the quantization error. Such a statistical analysis can identify the optimum shape and size of the geometric regions represented by the test strip calibration codes. The geometric regions thus identified can then be associated with, for example, a single test strip calibration code and distributed across the multi-dimensional calibration parameter space. Thereafter, any lot of test strips with experimentally measured calibration parameters that are within a given geometric region can be assigned the single test strip calibration code associated with that geometric region.

EXAMPLES

Example 1

Diagnostic Kit for Blood Glucose Measurement

Figure 2:
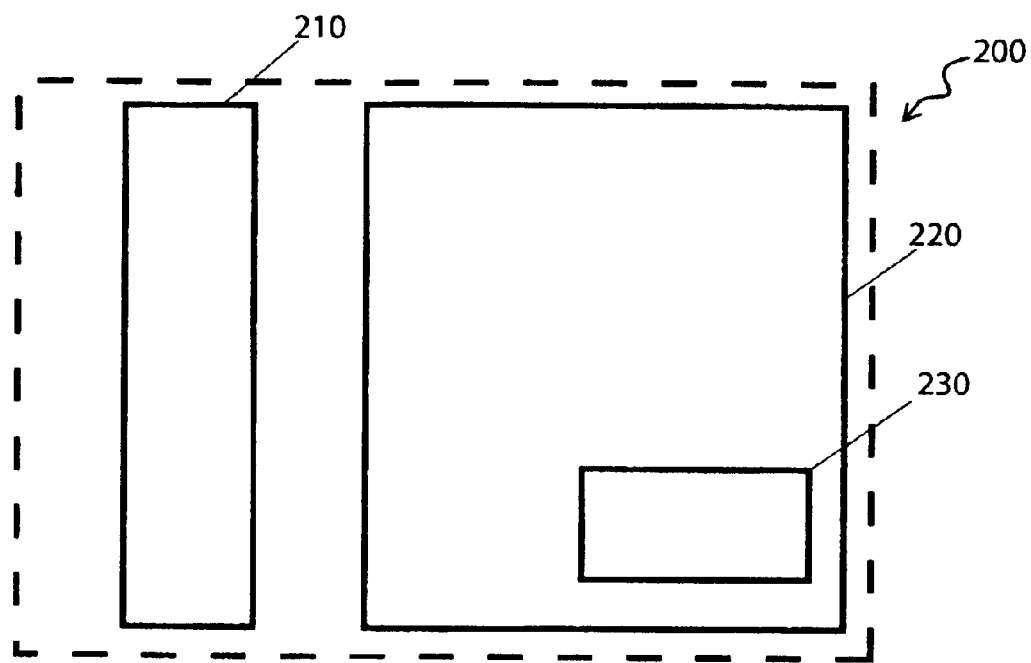
FIG. 2 is a simplified block diagram of a diagnostic kit according to another exemplary embodiment of the present invention.

An exemplary diagnostic kit 200 for blood glucose measurement according to the present invention includes a disposable blood glucose test strip 210 and a meter 220 (i.e., device) for measuring a property of the disposable blood glucose test strip, as illustrated in FIG. 2. The meter 220 is adapted to calculate the blood glucose concentration of a blood sample applied to the disposable blood glucose test strip 210 using an algorithm of the following simplified form:

$$G = I^p(C_0 - Z) \quad (1)$$

where:
G=blood glucose concentration;
I and $C_0$ are properties of disposable blood glucose test strip 210 (to which a fluid sample has been applied) measured by meter 220; and
p and Z are test strip calibration parameters.

Meter 220 includes a memory 230 storing a plurality of test strip calibration codes. Each of the plurality of test strip calibration codes represents a hexagonal geometric region of a two-dimensional p-Z calibration parameter space. In memory 230, the plurality of test strip calibration codes and hexagonal geometric regions are distributed across a two-dimensional p-Z calibration parameter space such that a quantization error of assigning one of the plurality of test strip calibration codes to the test strip is optimally minimized.

The optimized distribution of test strip calibration codes and hexagonal geometric regions across the two-dimensional p-Z calibration parameter space, and the benefits that are derived from this distribution, will be apparent to one skilled in the art based on the following description of the mathematical analysis technique used to obtain the optimized distribution and hexagonal shape of the geometric regions. First, equation (1) above was re-written as:

$$G(p,Z) = I^p(C_0 - Z) \quad (2)$$

Next, to facilitate the optimal reduction of the quantization error (i.e., to limit the error due to the assignment of a test strip calibration code to a lot of tests strips), the following two "constant error" equations (i.e., objective functions) were created:

$$|G(p, Z) - G(\bar{p}, \bar{Z})| = \varepsilon_a \quad (3)$$

$$\frac{|G(p, Z) - G(\bar{p}, \bar{Z})|}{G(\bar{p}, \bar{Z})} = \varepsilon_r$$

These constant error equations represent absolute and relative errors, respectively, due to test strip calibration code assignment. For diagnostic kit 200, the first "$\varepsilon_a$" equation applies for blood glucose concentrations of between 20 mg/dL and 100 mg/dL and the second "$\varepsilon_r$" equation applies for blood glucose concentrations from 100 mg/dL to 600 mg/dL. The "$\varepsilon_a$" equation is for an absolute error (2 mg/dL in this exemplary embodiment) and the "$\varepsilon_r$" equation is for a relative error (2% in this exemplary embodiment). The term G($\bar{p},\bar{Z}$) is the glucose equation for a fixed value of $\bar{p}$ and $\bar{Z}$ which are values taken from a calibration code table. The greater the difference between p and $\bar{p}$, and between Z and $\bar{Z}$, the greater the difference (or error) between a reported blood glucose concentration value, G($\bar{p}, \bar{z}$) and the actual blood glucose concentration value, G(p,Z).

The constant error equations above were based on two predetermined diagnostic kit accuracy requirements, namely that the diagnostic kit has an error of +/−10 mg/dL for blood glucose concentrations of between 20 mg/dL and 100 mg/dL and an error of +/−10% for blood glucose concentrations of greater than 100 mg/dL up to 600 mg/dL. However, since these requirements represent the total allowable error for the diagnostic kit, only a portion was allocated to the calibration error budget, namely:

$$\varepsilon_a = 2 \text{ mg/dL}; \quad (4)$$

and $$\varepsilon_r = 2\% \quad (5)$$

In practice, the p and Z values determined during calibration of a test strip lot can be used to assign a test strip calibration code ($\bar{p}$, $\bar{Z}$) to the lot of test strips. This assignment is based on the proximity of the measured p and Z to the test strip calibration code. The measure of proximity is the difference between the blood glucose concentration using the test strip calibration code and the blood glucose concentration glucose using the measured p, Z. That proximity is represented by the constant error equations above.

Figure 3:
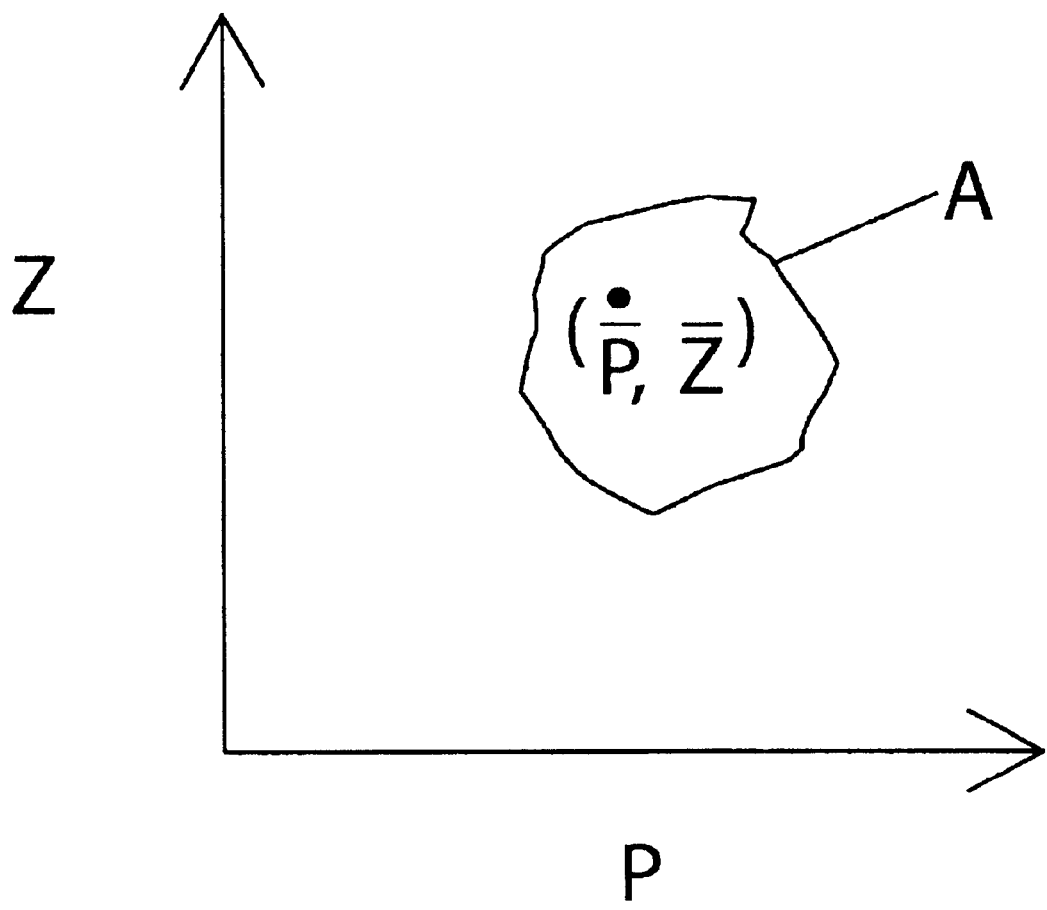
FIG. 3 is a sketch illustrating a boundary of maximum permissible error enclosing a geometric region of p and Z values in a p-Z calibration parameter space.

The set of p and Z values, which satisfy the two constant error equations above, define the boundary of maximum permissible error defined by $\varepsilon_a$ and $\varepsilon_r$. This results in an enclosed geometric region of p and Z values. For $\bar{p}$ and $\bar{Z}$ values within this geometric region, assignment to $\bar{p}$ and $\bar{Z}$ results in an error less than $\varepsilon_a$[absolute error] and less than $\varepsilon_r$[relative error]. FIG. 3 illustrates how the constant error equations define such a boundary. In FIG. 3, the closed curve "A" is the set of points that satisfy the constant error equations. Therefore, the points within the closed curve have errors less than the defined relative and absolute errors.

For diagnostic kit 200, the objective was to determine the shape of the geometric region around $\bar{p}$ and $\bar{Z}$ and how p, Z, I and $C_0$ effected that shape. From this, a determination was then made on how these geometric regions fit together so that a series of ($\bar{p}$, $\bar{Z}$) values could be generated as test strip calibration codes covering the p-Z calibration parameter space.

In order to make the constant error equations more tractable, G(p,Z) was expanded in a Taylor expansion and approximated by discarding terms higher than linear order, resulting in:

$$G(p, Z) = G(\bar{p}, \bar{Z}) + \frac{\partial G(p, Z)}{\partial p} \cdot (p - \bar{p}) + \frac{\partial G(p, Z)}{\partial Z} \cdot (Z - \bar{Z}) \quad (6)$$

where the partial derivatives are:

$$\frac{\partial G(p, Z)}{\partial p} = G_p = G(p, Z) \cdot \ln(I)$$

$$\frac{\partial G(p, Z)}{\partial Z} = G_Z = -I^p$$

Combining these back into the constant error equations resulted in:

$$\varepsilon_a = |G(p, Z) - G(\bar{p}, \bar{Z})| \quad (7)$$
$$= \left| \frac{\partial G(p, Z)}{\partial p} \cdot (p - \bar{p}) + \frac{\partial G(p, Z)}{\partial Z} \cdot (Z - \bar{Z}) \right|$$
$$= |G(\bar{p}, \bar{Z}) \cdot \ln(I) \cdot (p - \bar{p}) - I^{\bar{p}} \cdot (Z - \bar{Z})|$$

and $$\varepsilon_r = \frac{|G(\bar{p}, \bar{Z}) \cdot \ln(I) \cdot (p - \bar{p}) - I^{\bar{p}} \cdot (Z - \bar{Z})|}{G(\bar{p}, \bar{Z})} \quad (8)$$

These constant error equations (i.e., equations 7 and 8) were plotted on p, Z axes in a geometric region near $\bar{p}$, $\bar{Z}$.

Figure 4:
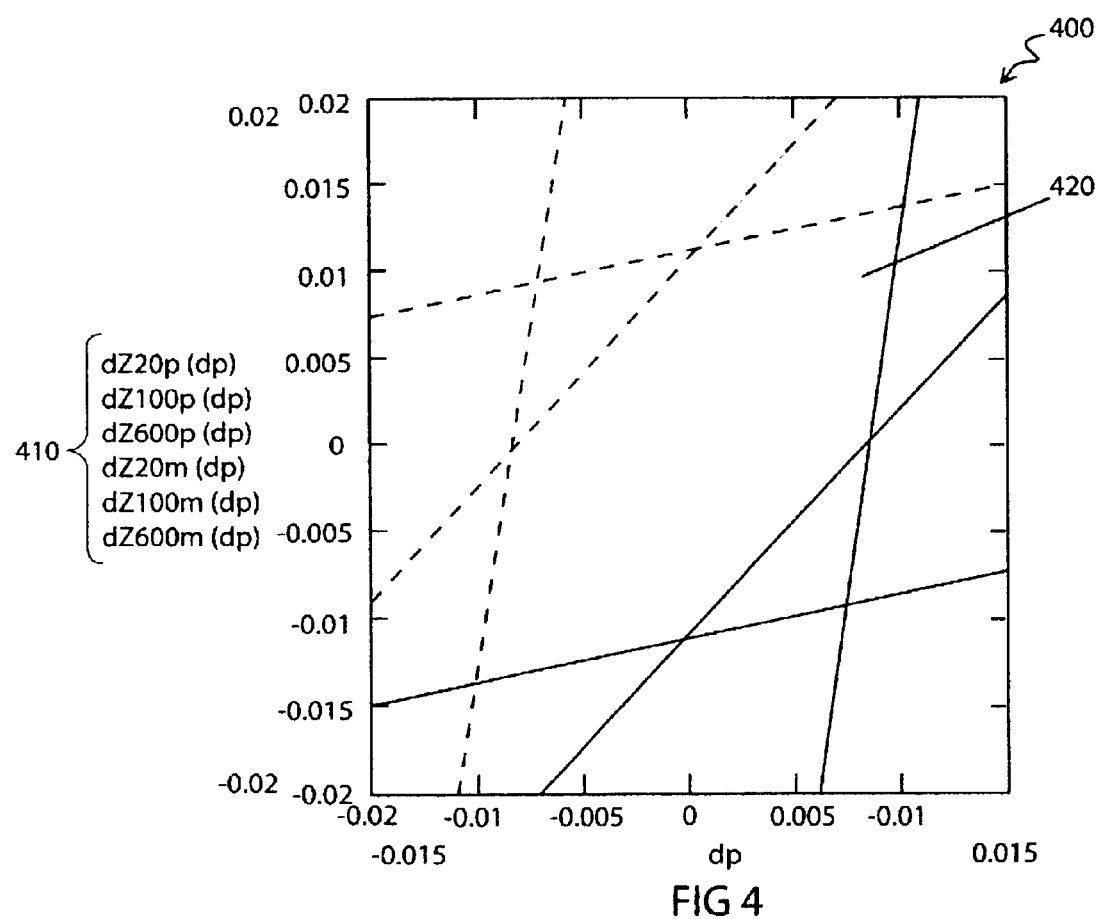
FIG. 4 is a graph illustrating the manner in which constant error equations can be plotted to define a bounded geometric region for representation by a test strip calibration code.

The result is illustrated in FIG. 4 where, for ease of graphing, the $\bar{p}$, $\bar{Z}$ have been chosen as (0,0). In order to define the calibration code geometric region, these equations must be considered for all permitted ranges of sample conditions. Certain values within the range of sample conditions will limit performance and thus define the geometric region. For this example, the limits occur at I=10, and glucose levels of 20 mg/dL, 600 mg/dL, and 100 mg/dL, which respectively correspond to the lowest glucose level, the highest glucose level, and the glucose level of transition between the two constant error equations. Due to absolute value signs (which give rise to two equations) and the three glucose level limits, the result was a series of six lines 410 which bound a hexagonal geometric region 420. These lines and the hexagonal geometric region 420 that the lines bound are illustrated in FIG. 4.

Based on the above description, one skilled in the art will recognize that the invention of Example 1 provides the optimum shape for each geometric region represented by a test strip calibration code based on the glucose algorithm equation (1), and the error equations (7) and (8), which are set relative to diagnostic kit performance (e.g., accuracy) requirements.

Example 2

Figure 5:
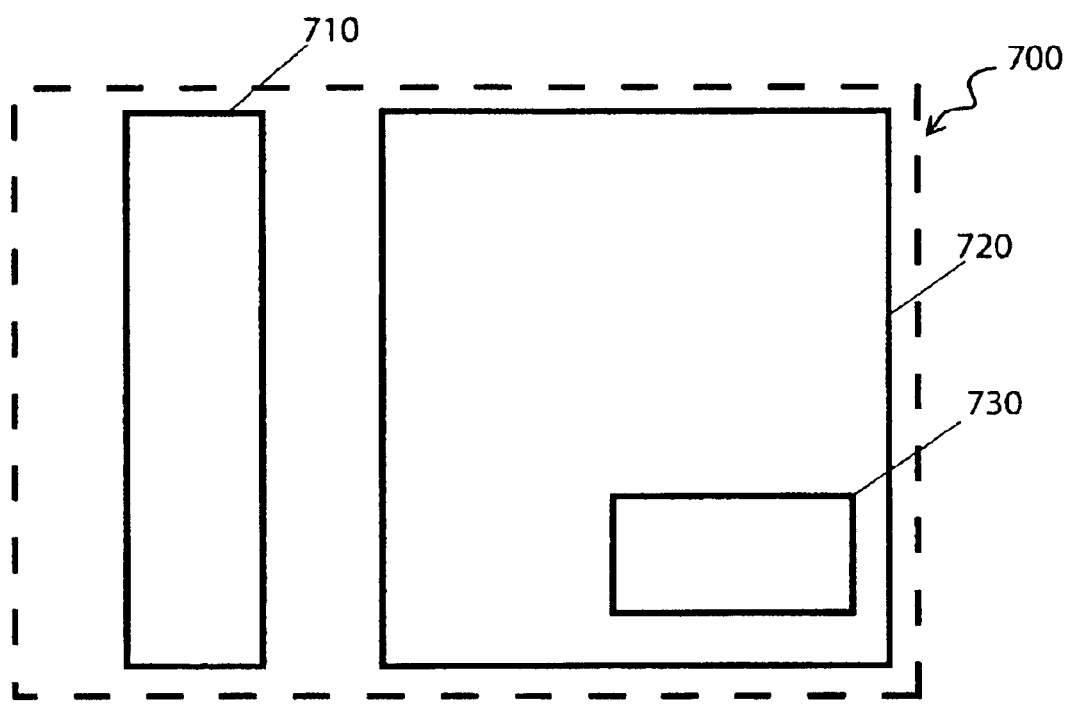
FIG. 5 is a simplified block diagram of a diagnostic kit according to yet another exemplary embodiment of the present invention.

Diagnostic Kit for Blood Glucose Measurement that Includes an Electrochemical Test Strip and Meter Device A diagnostic kit 700 (within the dashed lines) for blood glucose measurement includes an electrochemical test strip 710 and a device 720 (e.g., a hand-held meter) for measuring an electrochemical property of the electrochemical test strip 710, as illustrated in FIG. 5. Device 720 is adapted to calculate the blood glucose concentration of a blood sample applied to electrochemical test strip 710 using the algorithm of equation (1).

Device 720 includes a memory 730 storing thirty-three test strip calibration codes. Each of the plurality of test strip calibration codes represents a hexagonal geometric region or a partial hexagonal geometric region of a two-dimensional p-Z calibration parameter space. As is explained in more detail below, the two-dimensional p-Z calibration parameter space of this embodiment covers "Z" calibration parameters from 0.0 to 0.8 and "p" calibration parameters from 0.50 to 0.80.

The thirty-three test strip calibration codes (stored in memory 730) and hexagonal (or partial hexagonal) geometric regions are distributed across the two-dimensional p-Z calibration parameter space such that a quantization error of assigning one of the test strip calibration codes to the electrochemical test strip 710 is optimally reduced.

The following technique was employed to determine the distribution of test strip calibration codes and geometric regions across the p-Z calibration parameter space. First, it was recognized that the assignment of test strip calibration codes to calibration coefficients (i.e., p and Z) must be optimized in order to obtain an accurate blood glucose measurement with diagnostic kit 700. In other words, the quantization error must be optimally reduced. To optimally reduce the quantization error, a mean absolute bias (MAB) objective function was utilized. The MAB objective function was defined as follows:

$$MAB = \frac{\sum_{i=1}^{m} |Bias| + \sum_{i=1}^{n} |\% \, Bias|}{m+n} \quad (9)$$

where
Bias=G−YSI YSI≦100 mg/dL
% Bias=[(G−YSI)÷YSI]×100 YSI>100 mg/dL
and where G is defined in Equation (1) above;
  m is the number of strips tested with YSI glucose value <=100 mg/dL;
  n is the number of strips tested with YSI glucose value >100 mg/dL; and
  YSI=plasma glucose value measured using a standard Yellow Springs reference instrument.

In defining the MAB objective function, the mean of both absolute bias and percent (%) bias were combined together in a mixed unit fashion. This combination of biases was implemented to account for the heteroscedastic nature of the glucose response in diagnostic kit 700.

Twenty electrochemical test strip lots were then prepared that included purposely-introduced process variation. This purposely-introduced process variation was designed to mimic the process-induced variation that would be encountered throughout the manufacturing time period of the electrochemical test strips. For each electrochemical test strip lot, the optimal p and Z calibration parameters were experimentally determined by minimizing the MAB objective function. Based on the ranges of observed p and Z values, it was determined that the two-dimensional p-Z calibration parameter space would span "p" values from 0.5 to 0.8 and "Z" values from 0 to 0.8.

Once apprised of the present invention, one of ordinary skill in the art will recognize that the number of electrochemical test strip lots employed in evaluating the objective function can vary depending on the magnitude of the expected process variation and the degree of confidence needed when defining the calibration parameter space. In practice, the number of test strip lots will typically range from about 20 to 60 test strip lots for an initial definition the calibration parameter space.

Next, the calibration error of the p and Z calibration parameters due to blood donor, device and blood glucose concentration were determined for each electrochemical test strip lot. For example, the calibration error due to blood donor was determined by systematically removing data for one blood donor at a time and re-optimizing p and Z from the remaining data set. The minimum, maximum and range of the calibration error were determined for p and Z for each source of variation (i.e., blood donor, device and blood glucose concentration) per electrochemical test strip lot to determine the overall variability. The $95^{th}$ percentile of the error ranges for p and Z were then determined for a fixed test scheme over all the lots. This $95^{th}$ percentile for error in measurement of calibration coefficients was subsequently employed as an increment of resolution for examining the calibration parameter space. Based on the collected data, it was determined that the $95^{th}$ percentile of p=0.03 and that the $95^{th}$ percentile of Z=0.10. These $95^{th}$ percentile values were chosen as an increment of resolution for distributing test strip calibration codes across the p-Z calibration parameter space.

Figure 6:
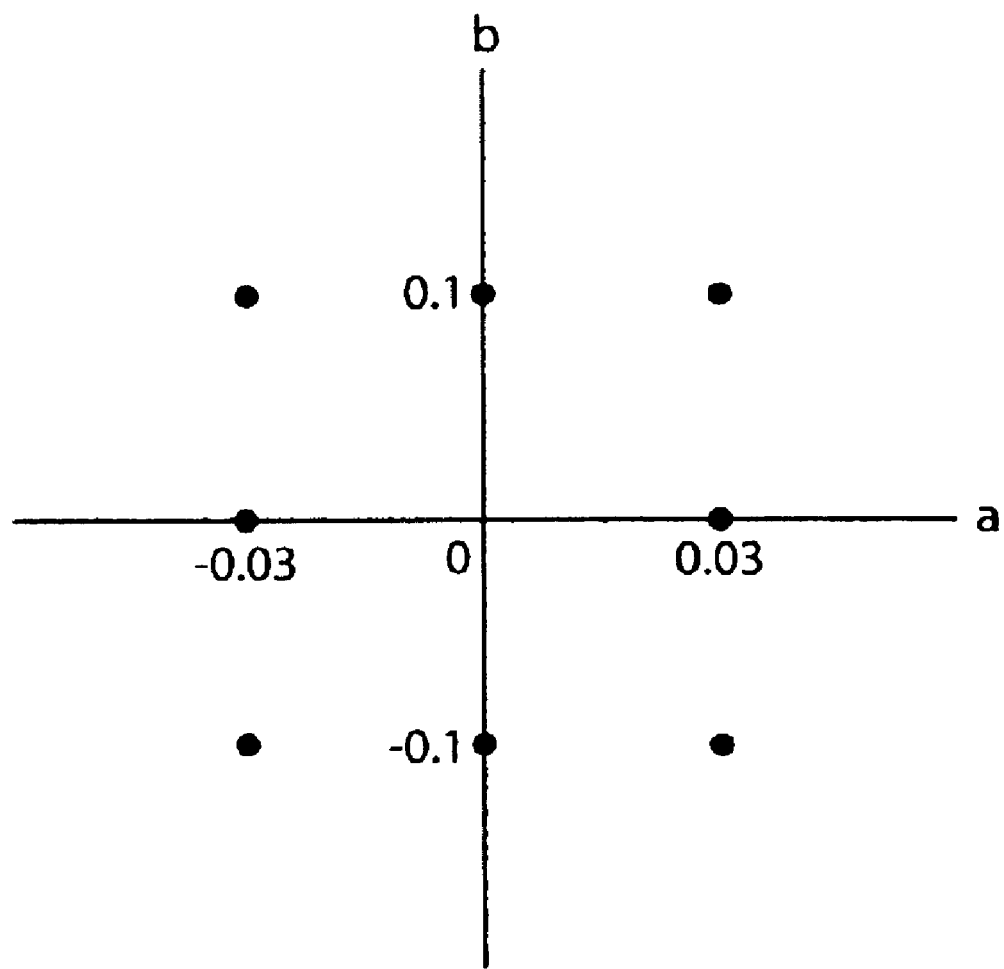
FIG. 6 is a graph depicting Cartesian coordinates for a perturbation matrix technique used in conjunction with the present invention.

A perturbation matrix technique was then employed to evaluate the MAB objective function. FIG. 6 is a Cartesian coordinate plot that shows the combination of p and Z calibration parameter values employed in the perturbation matrix. In other words, the MAB was recalculated for the following 8 combinations.

(0.03, 0): p=optimized p+0.03; and Z=optimized Z.
(−0.03, 0): p=optimized p−0.03; and Z=optimized Z.
(0, 0.1): p=optimized p; and Z=optimized Z+0.1.
(0, −0.1): p=optimized p; and Z=optimized Z−0.1.
(0.03, 0.1): p=optimized p+0.03; and Z=optimized Z+0.1
(−0.03, 0.1): p=optimized p−0.03; and Z=optimized Z+0.1
(0.03, −0.1): p=optimized p+0.03; and Z=optimized Z−0.1
(−0.03, −0.1): p=optimized p−0.03; and Z=optimized Z−0.1

Figure 7:
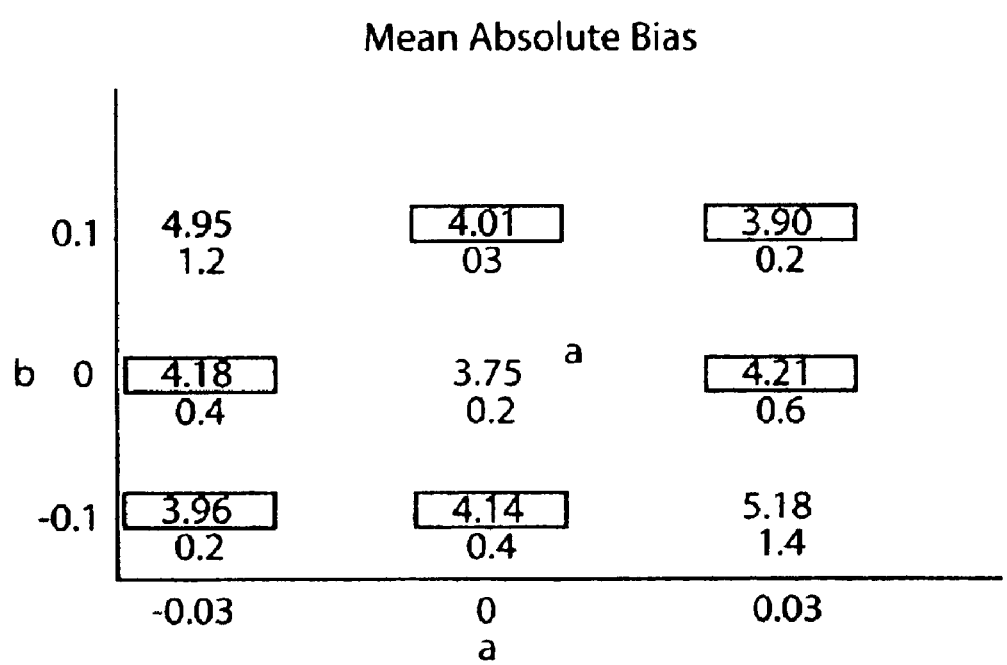
FIG. 7 is a graph depicting a perturbation matrix for an MAB objective function associated with a test strip in an example of the present invention.

The MAB value for each of the coordinates in FIG. 6 was subsequently calculated and plotted on a perturbation matrix for each of the twenty electrochemical test strip lots. In this example, the allowable quantization error was then set to 0.50 MAB. A review of the perturbation matrices indicated that the majority exhibited a hexagonal pattern in terms of meeting the 0.5 MAB quantization error limit (see FIG. 7 which depicts a table of MAB values for one of the twenty electrochemical test strip lots). Note that the italicized number below each MAB value represents the difference of new MAB from the original MAB at the origin. Enclosed in rectangular boxes are the MAB's that differ from the optimized p and Z by <=0.5. This hexagonal (honeycomb) pattern was, therefore, chosen as the basic shape for each geometric region represented by a test strip calibration code stored in memory 730.

Figure 8:
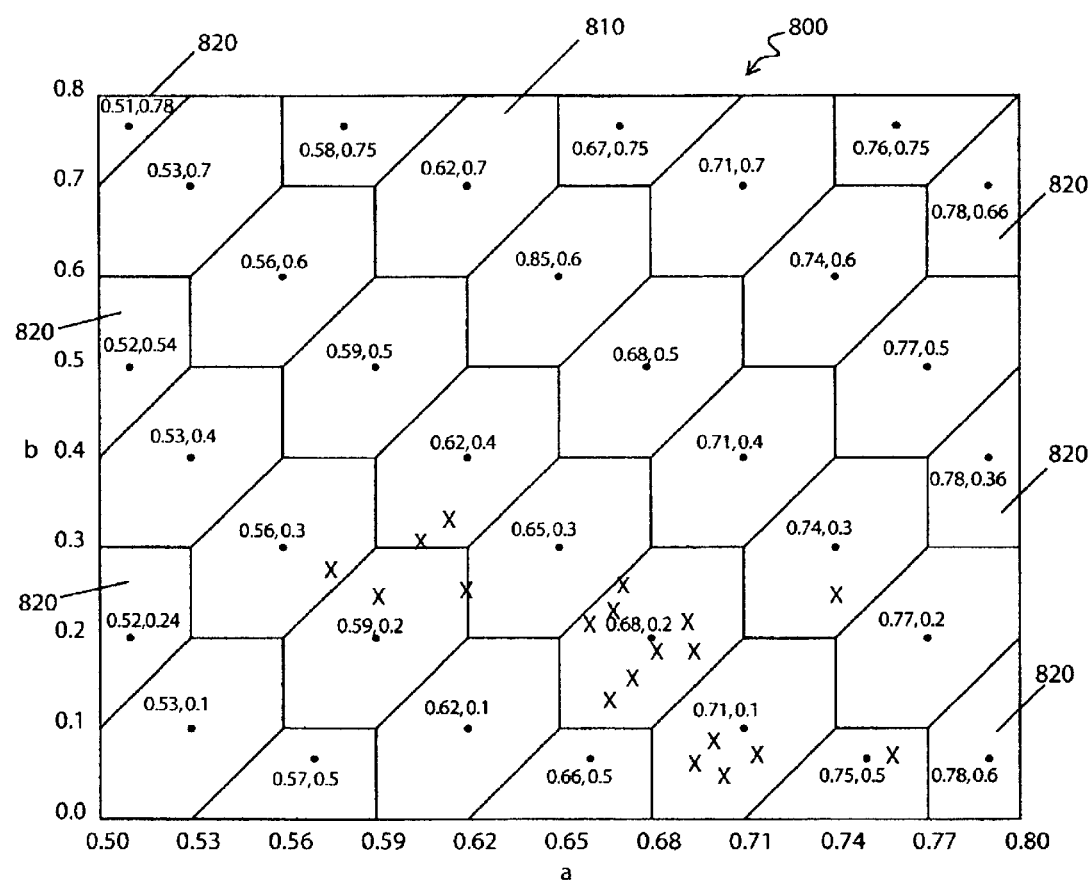
FIG. 8 is an illustration depicting a distribution of test strip calibration codes, and geometric regions represented thereby, across an p-Z calibration parameter space in an exemplary embodiment of the present invention.

The resulting p-Z calibration parameter space 800 is illustrated in FIG. 8. Using the increments of resolution of 0.03 and 0.10 and hexagonal shaped geometric regions, the thirty-three test strip calibration codes (depicted by filled circles in FIG. 8) and hexagonal geometric regions 810 were then distributed across the p-Z calibration parameter space 800, as shown in FIG. 8. Partial hexagonal geometric regions 820 were employed at edges of the p-Z calibration parameter space 800 where full hexagonal geometric regions would have extended beyond the edge. The distribution was initiated by assigning a test strip calibration code near the center of the p-Z calibration parameter space (i.e., the test strip calibration code and hexagonal geometric region assigned to p=0.62 and Z=0.40) followed by distribution of the test strip calibration codes and hexagonal geometric regions across the calibration parameter space at the defined increments of resolution. The calibration parameters assigned to each test strip calibration code are shown in parenthesis above each the filled circles that depict the test strip calibration codes.

The number of hexagonal and partial hexagonal geometric regions formed within the p-Z calibration parameter space indicates the total number of test strip calibration codes (i.e., thirty-three) required for diagnostic kit 700. Each respective test strip calibration code is defined as the midpoint of each polygonal geometric region (i.e., each hexagonal geometric region or partial hexagonal geometric region). The location of the optimized p and Z for the each of the twenty electrochemical test strip lots are marked by an X in FIG. 10.

Example 3

Figure 9:
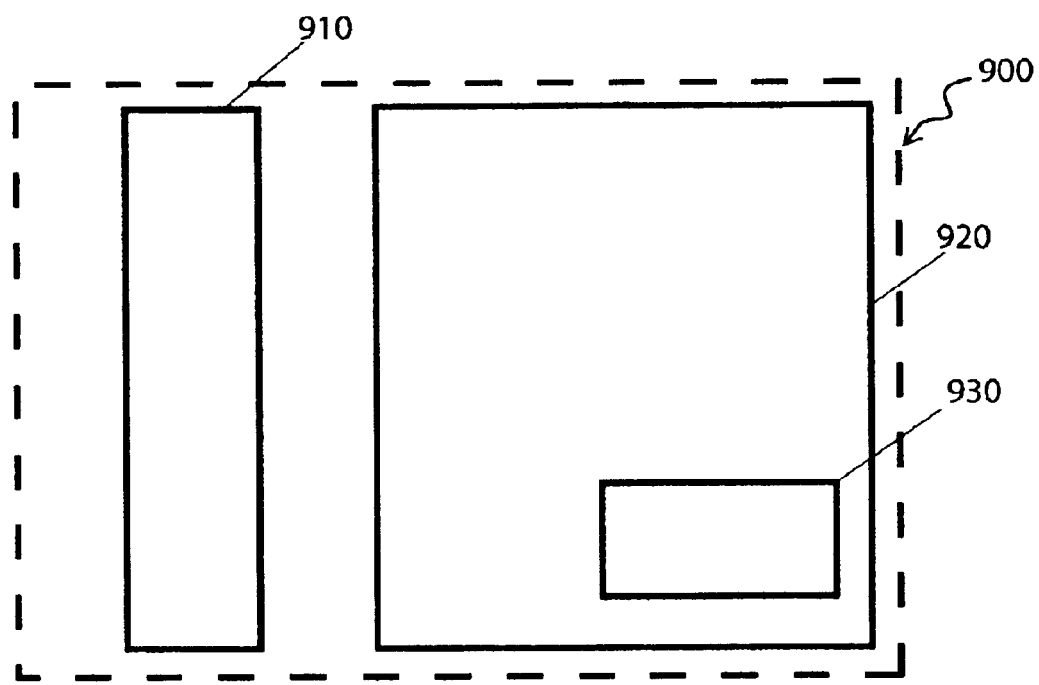
FIG. 9 is a simplified block diagram of a diagnostic kit according to yet another exemplary embodiment of the present invention.

Diagnostic Kit with a Photometric Test Strip and Meter for Prothrombin-Time (PT) and INR Measurements A diagnostic kit 900 for PT and INR measurement includes a test strip 910 and a device 920 (e.g., a hand-held meter) for measuring optical properties of the test strip 910, as illustrated in FIG. 9. Device 920 is adapted to calculate the International Normalization Ratio (INR) of a blood sample applied to test strip 910 using the following algorithm:

$$INR = \left(\frac{PT}{MNPT}\right)^{ISI} \quad (10)$$

where:
PT is a prothrombin time measured by device 920; and
MNPT and ISI are calibration parameters.

Device 920 includes a memory 930 storing fourteen test strip calibration codes, each representing a polygonal geometric region of an MNPT-ISI calibration parameter space. As is explained in more detail below, the MNPT-ISI calibration parameter space of Example 3 covers MNPT calibration parameters from 7.04 to 9.07 and ISI calibration parameters from 0.99 to 1.32.

In memory 930, the fourteen test strip calibration codes and polygonal geometric regions are distributed across the two-dimensional MNPT-ISI calibration parameter space such that a quantization error of assigning one of the test strip calibration codes to the test strip 910 is optimally reduced.

In diagnostic kit 900, test strip 910 has been assigned a test strip calibration code based upon its experimentally-determined ISI and MNPT calibration parameters. Each test strip 910 requires a test strip calibration code with fixed ISI and MNPT calibration parameters. Such fixed ISI and MNPT calibration parameters enable a user to convey a test strip calibration code to device 920 so that device 920 can employ the ISI and MNPT calibration parameters that correspond to the test strip calibration code in computation of INR.

Figure 10:
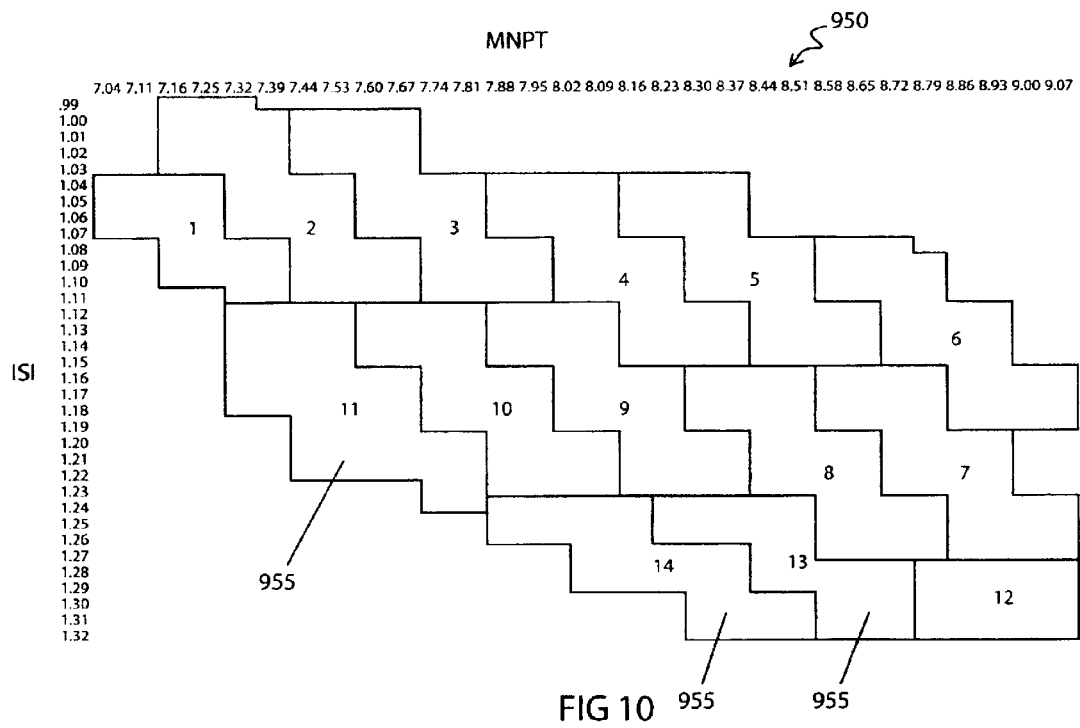
FIG. 10 is an illustration depicting a distribution of test strip calibration codes, and stepped polygonal geometric regions represented thereby, across an MNPT-ISI calibration parameter space in an exemplary embodiment of the present invention.

Based on experimental data, the MNPT-ISI calibration parameter space for diagnostic kit 900 was initially conceived as a rectangular space with ISI values ranging between 0.99 and 1.32 and MNPT values ranging between 7.04 and 9.07. However, this rectangular calibration parameter space was then limited to a diagonal MNPT-ISI calibration parameter space (as illustrated in FIG. 10 and described further below) within the rectangular space. This limitation was based on a diagnostic kit accuracy requirement that INR measurements results within the entire MNPT-ISI calibration parameter space should not differ by more than 25%.

To estimate the calibration error associated with the ISI and MNPT calibration parameters, their 95% confidence intervals were computed. In this example, the ISI and MNPT calibration parameters follow a normal distribution. Therefore, the confidence intervals were computed directly by applying parametric statistics. The half-width of the 95% confidence interval for ISI and MNPT had mean width of 0.045 and 0.38 respectively. This result indicated that an ISI width of 0.09 and an MNPT width of 0.76 should result in similar diagnostic kit performance. However, it was known that the performance of the diagnostic kit remained acceptable with increasing ISI and MNPT since these calibration parameters have opposing influence on the INR measurement.

Based on the above analysis, the fourteen test strip calibration codes were assigned to polygonal geometric regions within the MNPT-ISI calibration parameter space that were essentially diagonal in overall shape with each polygonal geometric region have a "stepped" outline. FIG. 10 depicts the resulting calibration parameter space 950 across which fourteen test strip calibration codes (1–14) and fourteen stepped polygonal geometric regions 955 have been distributed. The stepped polygonal geometric regions 955 can be viewed as a combination of adjacent parallelograms.

The following technique was then employed to determine the distribution of the fourteen test strip calibration codes and polygonal geometric regions across the MNPT-ISI calibration parameter space in memory 930. To optimally reduce the quantization error, both absolute difference and relative difference objective functions were employed. These functions took the following forms:

I. AbsoluteDifference=|Patient_INR−Reference_INR|

II. $AbsoluteRelativeDifference = \left( \frac{|Patient\_INR\_Reference\_INR|}{Reference\_INR} \right) * 100$ where:

Patient_INR is the INR response obtained by the diagnostic kit; and

Reference_INR is the INR response obtained by a reference measurement system.

The following two diagnostic kit accuracy requirements were also considered in distributing the test strip calibration codes and polygonal geometric regions across the MNPT-ISI calibration parameter space:

(a) The mean absolute relative deviation (MARD), i.e., mean of absolute relative difference across patient population for total diagnostic kit accuracy across the assay range shall be less than 15% when the correct test strip calibration code is used; and (b) For a statistically relevant sample size, 95% of paired values shall be within ±1.0 INR. This requirement can be ascertained if $95^{th}$ percentile of Absolute Differences is less than 1.0 INR.

There are two performance metrics in this example, with MARD being employed as the primary metric and the $95^{th}$ Percentile of Paired Difference employed as the secondary metric in determining the extent of the ISI-MNPT calibration parameter space and the size and shape of each geometric region represented by a test strip calibration code. The extent of the ISI-MNPT calibration parameter space and size of the geometric regions was determined using the primary metric and verified with the second metric. The MARD and $95^{th}$ Percentile of Paired Differences with optimal ISI and MNPT were in the range of 4 to 7.5 and 0.2 to 0.45 respectively for an experimental data set.

FIG. 10 illustrates the manner in which the fourteen test strip calibration codes and fourteen stepped polygonal geometric regions 955 were distributed across the ISI-MNPT calibration parameter space 950 in memory 930. One skilled in the art will recognize that memory 930 can store such a distribution using conventional methods. For example, memory 930 could include a table, such as Table 1 below, associating test strip calibration codes (e.g., 1–14) to MNPT calibration parameters (e.g., $A_1$–$A_{14}$) and ISI calibration parameters (e.g., $B_1$–$B_{14}$).

TABLE 1

| Test Strip Calibration Code | MNPT Calibration Parameter | ISI Calibration Parameter |
|---|---|---|
| 1 | $A_1$ | $B_1$ |
| 2 | $A_2$ | $B_2$ |
| 3 | $A_3$ | $B_3$ |

TABLE 1-continued

| Test Strip Calibration Code | MNPT Calibration Parameter | ISI Calibration Parameter |
|---|---|---|
| 4 | $A_4$ | $B_4$ |
| 5 | $A_5$ | $B_5$ |
| 6 | $A_6$ | $B_6$ |
| 7 | $A_7$ | $B_7$ |
| 8 | $A_8$ | $B_8$ |
| 9 | $A_9$ | $B_9$ |
| 10 | $A_{10}$ | $B_{10}$ |
| 11 | $A_{11}$ | $B_{11}$ |
| 12 | $A_{12}$ | $B_{12}$ |
| 13 | $A_{13}$ | $B_{13}$ |
| 14 | $A_{14}$ | $B_{14}$ |

Figure 11:
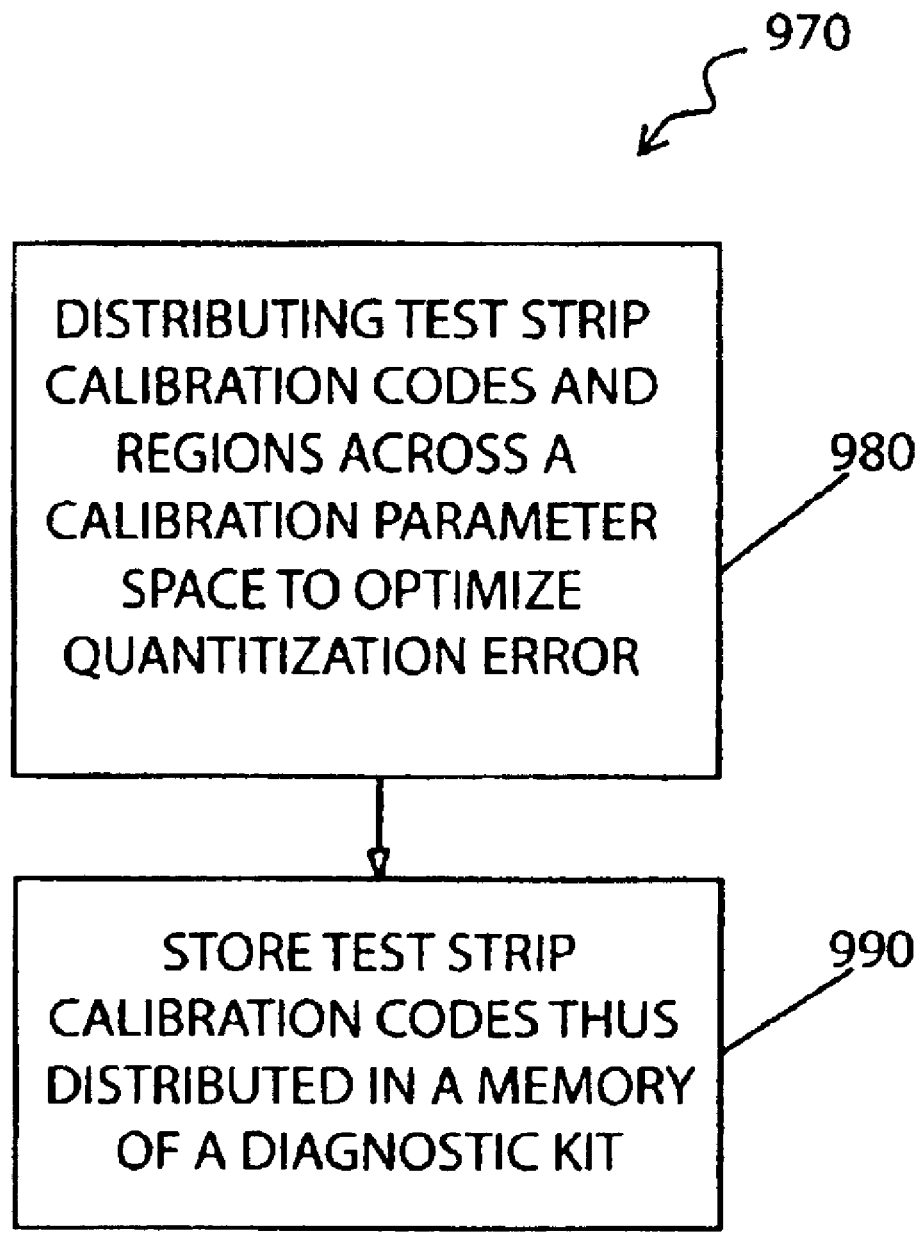
FIG. 11 is a flow diagram illustrating a sequence of steps in a process according to one exemplary embodiment of the present invention.

FIG. 11 is a flow diagram illustrating a sequence of steps in an exemplary method 970 according to the present invention for optimally associating test strip calibration codes to calibration parameters for use in a diagnostic kit that includes a test strip and a device with a memory.

Method 970 includes distributing a plurality of test strip calibration codes and geometric regions represented by the plurality of calibration codes across a calibration parameter space, as set forth in step 980. The distribution is conducted such that a quantization error of assigning one of the plurality of test strip calibration codes to the test trip of the diagnostic kit is optimally reduced. The distribution of the plurality of test strip calibration codes and geometric regions serves to associate each of the plurality of test strip calibration codes with calibration parameters of the calibration parameter space.

The calibration parameter space can be any suitable calibration parameter space known to one skilled in the art. For example, the calibration parameter space can be a multi-dimensional calibration parameter space such as the p-Z calibration parameter and an MNPT-ISI calibration parameter spaces described above in Diagnostic kit Examples 2 and 3.

The quantization error can be optimally reduced using any mathematical, statistical (e.g., constant error equation techniques) or experimental technique (such a perturbation matrix techniques employing MAB objective functions) known to one skilled in the art. As described with regard to Examples 1, 2 and 3 above, it can be especially beneficial to optimally reduce the quantization error using an objective function (e.g., MAB, MARD or constant error equation(s)).

Method 970 also includes the step of storing the plurality of test strip calibration codes thus distributed in a memory of the diagnostic kit, as set forth in step 990. This storage can take the form of a table or other software implementation known to one of ordinary skill in the art and can be accomplished using any suitable storage technique.

Since methods and diagnostic kits according to the present invention provide for a minimal number of test strip calibration codes, they enable a practical evaluation of a test strip lot using each of the plurality of test strip calibration codes and experimental data collected on the test strip lot. The test strip calibration code which minimizes error (based, for example, on an objective function such as MAB) could then be assigned to the test strip lot.

It is contemplated that the exemplary method described above can be adapted by one skilled in the art to optimally associate reagent calibration codes to calibration parameters for use in assay kits that includes a reagent and an analytical device with a memory. In such a circumstance, the resulting method would include distributing a plurality of reagent calibration codes and geometric regions represented by the reagent calibration codes across a calibration parameter space such that a quantization error of assigning one of the reagent calibration codes to the reagent is optimally reduced. In doing so, the reagent calibration codes would be associated with calibration parameters of the calibration parameter space. The method would also include storing the reagent calibration codes thus distributed in a memory of the analytical device.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. A diagnostic kit for measuring a characteristic of a fluid sample, the diagnostic kit comprising:
   a test strip with a test strip calibration code assigned thereto; and
   a device for measuring at least one property of the test strip and calculating, therefrom, a characteristic of a fluid sample applied to the test strip, the device including:
       a memory with a plurality of test strip calibration codes, including the test strip calibration code assigned to the test strip, stored therein, wherein each of the test strip calibration codes in the memory are mathematically manipulated in the device to represent a geometric region of a calibration parameter space, wherein the geometric regions are formed by a boundary of a set of points representing values of calibration parameters of maximum permissible error, and wherein the test strip calibration codes and geometric regions are distributed across the calibration parameter space such that a quantization error of having assigned the test strip calibration code to the test strip is optimally reduced.

2. The diagnostic kit of claim 1, wherein each of the test strip calibration codes represents a geometric region of a multi-dimensional calibration parameter space.

3. The diagnostic kit of claim 1, wherein the test strip is a disposable blood glucose test strip and wherein the device employs an algorithm of the simplified form:

$$G = I^p(C_0 - Z)$$

where:
   G=blood glucose concentration;
   I and $C_0$ are measured properties of the test strip; and
   p and Z are calibration parameters;
   to calculate blood glucose concentration and wherein the test strip calibration codes represent hexagonal geometric regions of a two-dimensional p-Z calibration parameter space.

4. The diagnostic kit of claim 3, wherein the test strip calibration codes are distributed across the two-dimensional p-Z calibration parameter space based on optimization using constant error equations.

5. The diagnostic kit of claim 3, wherein the test strip calibration codes represent one of hexagonal geometric regions and partial hexagonal geometric regions of the two-dimensional p-Z calibration parameter space.

6. The diagnostic kit of claim 5, wherein the test strip calibration codes are distributed across the two-dimensional conceptual p-Z calibration parameter space using an incremental resolution based on the 95th percentiles of a calibration parameter calibration error.

7. The diagnostic kit of claim 1, wherein the test strip is an International Normalization Ratio (INR) test strip and wherein the device employs an algorithm of the form:

$$INR = \left(\frac{PT}{MNPT}\right)^{ISI}$$

where:
   PT is a prothrombin time measured by the device; and
   MNPT and ISI are calibration parameters
to calculate INR and wherein the test strip calibration codes represent polygonal geometric regions of a two-dimensional MNPT-ISI calibration parameter space.

8. The diagnostic kit of claim 7, wherein the test strip calibration codes represent stepped polygonal geometric regions of the two-dimensional ISI-MNPT calibration parameter space.

9. The diagnostic kit of claim 8, wherein the stepped polygonal geometric regions are comprised of a plurality of adjacent parallelograms.

10. The diagnostic kit of claim 1, wherein the memory stores a plurality of test strip calibration codes that optimally reduce the quantization error by maintaining predetermined quantization error limits with a minimum number of test strip calibration codes.

11. The diagnostic kit of claim 10, wherein the predetermined quantization error limits are based on an accuracy requirement of the diagnostic kit.

12. The diagnostic kit of claim 1, wherein each of the test strip calibration codes represents one of a hexagonal geometric region or a partial hexagonal geometric region of a two-dimensional calibration parameter space.

13. The diagnostic kit of claim 1, wherein the memory stores a plurality of test strip calibration codes distributed such that each of the test strip calibration codes represent a polygonal geometric region of a two-dimensional calibration parameter space.

14. The diagnostic kit of claim 13, wherein the polygonal geometric region is a stepped polygonal geometric region comprised of a plurality of adjacent parallelograms.

15. The diagnostic kit of claim 1, wherein the test strip is a disposable blood glucose test strip and the device is a hand-held meter for measuring an optical property of the disposable blood glucose test strip.

16. The diagnostic kit of claim 1, wherein the test strip is a disposable blood glucose test strip and the device is a hand-held meter for measuring an electrochemical property of the disposable blood glucose test strip.

17. The diagnostic kit of claim 1, wherein the test strip is a prothrombin test strip and the device is a device for measuring optical properties of the prothrombin test strip.

18. The diagnostic kit of claim 1, wherein the test strip calibration codes are distributed across the calibration parameter space further using a geometric pattern that is dependent on an objective function that defines overall test strip calibration error.

19. The diagnostic kit of claim 1, wherein the device is a hand-held meter.

20. The diagnostic kit of claim 1, wherein the fluid sample is a physiological fluid sample.

21. A method for optimally associating test strip calibration codes to calibration parameters for use in a diagnostic kit that includes a test strip, with a test strip calibration code assigned thereto, and a device with a memory, the method comprising:
   mathematically manipulating a plurality of test strip calibration codes, including the test strip calibration code assigned to the test strip, in the device to represent geometric regions of a calibration parameter space, wherein the geometric regions are formed by a boundary of a set of points representing values of calibration parameters of maximum permissible error, distributing said plurality of test strip calibration codes and geometric regions represented by the test strip calibration codes across said calibration parameter space such that a quantization error of having assigned the test strip calibration code to the test strip is optimally reduced, thereby associating the test strip calibration codes with calibration parameters of the calibration parameter space; and storing the test strip calibration codes thus distributed in the memory of the device.

22. The method of claim 21, wherein the distributing step distributes the test strip calibration codes across a multi-dimensional calibration parameter space.

23. The method of claim 21, wherein the distributing step distributes a plurality of test strip calibration codes that represent one of a hexagonal geometric region or a partial hexagonal geometric region of a two-dimensional calibration parameter space.

24. The method of claim 21, wherein the distributing step distributes a plurality of test strip calibration codes that represent polygonal geometric regions of a two-dimensional calibration parameter space.

25. The method of claim 24, wherein the distributing step distributes a plurality of test strip calibration codes that are associated with stepped polygonal geometric regions of a two-dimensional calibration parameter space.

26. The method of claim 21, wherein the distributing step distributes a plurality of test strip calibration codes by optimally reducing the quantization error based on an objective function related to performance of the diagnostic kit.

27. The method of claim 21, wherein the distributing step distributes a plurality of test strip calibration codes by optimally reducing the quantization error based on a Mean Absolute Bias (MAB) objective function.

28. The method of claim 21, wherein the distributing step distributes a plurality of test strip calibration codes by optimally reducing the quantization error based on constant error objective functions related to performance of the diagnostic kit.

29. The method of claim 21, wherein the distributing step distributes a plurality of test strip calibration codes by optimally reducing the quantization error based on a Mean Absolute Relative Deviation (MARD) objective function.

30. An assay kit for analyzing a sample, the assay kit comprising:

a reagent; and an analytical device employed in conjunction with the reagent to carry out a predetermined analysis of the sample, the analytical device including:

a memory with a plurality of reagent calibration codes stored therein, wherein each of the reagent calibration codes in the memory are mathematically manipulated in the device to represent a geometric region of a calibration parameter space, wherein the geometric regions are formed by a boundary of a set of points representing values of calibration parameters of maximum permissible error, and wherein the reagent calibration codes and geometric regions are distributed across the calibration parameter space such that a quantization error of having assigned one of the reagent calibration codes to the reagent is optimally reduced.

31. A method for optimally associating reagent calibration codes to calibration parameters for use in an assay kit that includes a reagent and an analytical device with a memory, the method comprising:

mathematically manipulating a plurality of reagent calibration codes in the device to represent geometric regions of a calibration parameter space, wherein the geometric regions are formed by a boundary of a set of points representing values of calibration parameters of maximum permissible error, distributing said plurality of reagent calibration codes and geometric regions represented by the reagent calibration codes across said calibration parameter space such that a quantization error of having assigned one of the reagent calibration code to the reagent is optimally reduced, thereby associating the reagent calibration codes with calibration parameters of the calibration parameter space; and storing the reagent calibration codes thus distributed in the memory of the analytical device.

* * * * *